US010655061B2

(12) United States Patent
Saikia et al.

(10) Patent No.: US 10,655,061 B2
(45) Date of Patent: May 19, 2020

(54) PROCESS FOR THE PREPARATION OF BLUE-FLOURESCENCE EMITTING CARBON DOTS (CDTS) FROM SUB-BITUMINOUS TERTIARY HIGH SULFUR INDIAN COALS

(71) Applicant: Council of Scientific & Industrial Research, New Delhi, Delhi (IN)

(72) Inventors: Binoy Kumar Saikia, Assam (IN); Tonkeswar Das, Assam (IN); Sonali Roy, Assam (IN); Bardwi Narzary, Assam (IN); Hari Prasanna Dekaboruah, Assam (IN); Manobjyoti Bordoloi, Assam (IN); Jiumoni Lahkar, Assam (IN); Dipankar Neog, Assam (IN); Danaboyina Ramaiah, Assam (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 323 days.

(21) Appl. No.: 15/704,364

(22) Filed: Sep. 14, 2017

(65) Prior Publication Data

US 2018/0251678 A1 Sep. 6, 2018

(30) Foreign Application Priority Data

Mar. 2, 2017 (IN) .............................. 201711007354

(51) Int. Cl.
| | | |
|---|---|---|
| *C09K 11/65* | (2006.01) | |
| *C01B 32/184* | (2017.01) | |
| *C09D 5/22* | (2006.01) | |
| *G01N 33/58* | (2006.01) | |
| *C01B 32/15* | (2017.01) | |
| *C09D 7/40* | (2018.01) | |
| *C01B 32/20* | (2017.01) | |
| *B82Y 40/00* | (2011.01) | |
| *B82Y 20/00* | (2011.01) | |
| *C08K 3/04* | (2006.01) | |

(52) U.S. Cl.
CPC .............. *C09K 11/65* (2013.01); *C01B 32/15* (2017.08); *C01B 32/184* (2017.08); *C01B 32/20* (2017.08); *C09D 5/22* (2013.01); *C09D 7/67* (2018.01); *G01N 33/582* (2013.01); *G01N 33/587* (2013.01); *B82Y 20/00* (2013.01); *B82Y 40/00* (2013.01); *C01P 2004/64* (2013.01); *C01P 2006/60* (2013.01); *C08K 3/04* (2013.01); *Y10S 977/734* (2013.01); *Y10S 977/774* (2013.01); *Y10S 977/842* (2013.01); *Y10S 977/90* (2013.01); *Y10S 977/92* (2013.01); *Y10S 977/95* (2013.01)

(58) Field of Classification Search
CPC .. C09K 11/65; C09D 7/67; C09D 5/22; C01P 2004/64; C01P 2006/60; B82Y 40/00; B82Y 20/00; Y10S 977/734; Y10S 977/774; Y10S 977/842; Y10S 977/90; Y10S 977/95; Y10S 977/92; C08K 3/04; G01N 33/587; G01N 33/582; C01B 32/20; C01B 32/184; C01B 32/15
See application file for complete search history.

(56) References Cited

U.S. PATENT DOCUMENTS

2016/0060122 A1* 3/2016 Tour ...................... C01B 32/194
423/415.1

OTHER PUBLICATIONS

Chou, Chapter 2: Geochemistry of Sulfur in Coal, Orr and White; Geochemistry of Sulfur in Fossil Fuels ACS Symposium Series, American Chemical Society, pp. 30-52 (1990) (Year: 1990).*

* cited by examiner

*Primary Examiner* — Daniel C. McCracken
(74) *Attorney, Agent, or Firm* — Katten Muchin Rosenman LLP

(57) ABSTRACT

The present invention relates to a process for the preparation of blue-fluorescence emitting carbon dots (CDTs) from sub-bituminous tertiary high sulfur Indian coals. More particularly, the present invention relates to the production of characteristics carbon dots from low-quality Indian coals by an ultrasonic-assisted wet-chemical method. Also, the present invention provides a simple and environmentally benign method for fabrication of characteristics and size-controlled carbon dots.

13 Claims, No Drawings

PROCESS FOR THE PREPARATION OF BLUE-FLOURESCENCE EMITTING CARBON DOTS (CDTS) FROM SUB-BITUMINOUS TERTIARY HIGH SULFUR INDIAN COALS

FIELD OF THE INVENTION

The present invention relates to a process for the preparation of blue-fluorescence emitting carbon dots (CDTs) from sub-bituminous tertiary high sulfur Indian coals. More particularly, the present invention relates to the production of carbon dots from low-quality Indian coals by an ultrasonic-assisted wet-chemical method.

BACKGROUND OF THE INVENTION AND DESCRIPTION OF PRIOR ART

Coal is considered as a feedstock for carbon-based materials. Carbon nanomaterials (CNMs) have been gaining tremendous attention due to their wide range of applications in various fields. CNMs include carbon nanotubes, fullerenes, carbon dots, nanofibers, nanodiamonds, graphene nanosheets, graphene onions, etc. Among them, carbon dots (CDTs) are the newly emerging carbon nanomaterials, mainly including carbon quantum dots (CQDTs), less than 10 nm in size, graphene quantum dots (GQDTs) and graphene nanosheets with a plane size less than 100 nm. Carbon dots show many outstanding advantages such as low cost, low toxicity, robust, optical/chemical inertness, and a case of fabrication. Carbon dots have great potential application in various fields, including bio-imaging, cell-imaging, sensing, photovoltaic devices and catalysis.

Carbon-based dots have been fabricated from various carbon sources including fullerenes, glucose, graphite, graphene oxide, carbon nanosheets, biomass, and carbon fibers. Physical approaches such as lithography have also been used to fabricate graphene quantum dots from various carbon sources. However, current methods for the production of carbon dots suffer from numerous limitations. For instance, lithography techniques are expensive and impractical for the production of bulk quantities of carbon dots. Likewise, current carbon-based materials that are utilized for the production of carbon dots can be expensive in bulk quantities. Moreover, current methods of production carbon dots may not be able to control the size of the formed carbon dots. Therefore, new methods are required for the bulk production of carbon dots in a controlled manner.

Mineral acid solutions (Conc. $H_2SO_4$ and $HNO_3$) are tested as an oxidizing agent by the facile one-step wet-chemical method to fabricate carbon dots. However, it is found that the process is explosive, time-consuming and formation of sodium salts ($NaNO_3$) take place during the neutralization step by sodium hydroxide or ammonia solution, which is difficult to separate from the reaction media. Moreover, large quantities of water are needed instead of sodium hydroxide and ammonia solution during the neutralization step.

The related prior art references so far available in the literature for the production of carbon dots from coal are provided herein below.

Reference may be made to Nature Communication, 2013, 4:2943 (doi: 10.1038/ncomms3943) entitled "Coal as an abundant source of graphene quantum dots" which reports a facile one-step chemical method to synthesize tunable graphene quantum dots from various types of coal and coke samples. They have used mineral acids such as $HNO_3$ and $H_2SO_4$ for producing quantum dots from bituminous coals. Detailed characterization of the produced graphene quantum dots were examined by using analytical techniques. In this work, the graphene quantum dots were synthesized from bituminous coal, coke, and anthracite coal. However, in the present invention, the method as well as the characteristics of product differs from this report with respect to the use of reagents, techniques (ultrasonication, filtration, dialysis etc.) and other product characteristics.

Reference may be made to the article in Nanoscale, 2014, 6, 7410-7415 entitled "Graphene quantum dots, graphene oxide, carbon quantum dots and graphite nanocrystals in coals". This paper reports the preparation of single-layer graphene quantum dots (S-GODS) from six coal samples of different ranks by chemical oxidation and centrifugation methods using mineral acids ($HNO_3$ and $H_2SO_4$). The products were characterized by TEM, AFM, XRD, Raman and FTIR. However, the process reported therein is not similar to the present method in that the cited art had used strong mineral acids in the synthesis and the product characteristics were not described in detail.

Reference may be made to ACS Appl. Mater. Interfaces, 2015, 7, 7041-7048 entitled "Bandgap Engineering of Coal-Derived Graphene Quantum Dots" in which bandgaps of photo luminescent graphene quantum dots (GQDs) synthesized from anthracite coal was engineered by the one-step chemical oxidative treatment (using $HNO_3$ and $H_2SO_4$) at higher temperature or separation by cross-flow ultrafiltration. The products were characterized by TEM, DLS, XPS, Mass Spectroscopy, FTIR, $C^{13}$ NMR, UV-visible, XRD, Photoluminescence, and Raman analysis. The average sizes of the GQDTs were found to be 4.5±1.2, 16±3.3, 41±6.4, and 70±15 nm. However, the present invention differs in the process from the stated art with respect to the use of $H_2O_2$ and ultra-sonication. They had also used inorganic acids, which is not eco-friendly. Also, the report mainly emphasizes on the band-gap engineering of the quantum dots.

Reference may be made to ACS Nano, 2014, 8 (10), 10837-10843 entitled "Boron- and Nitrogen-Doped Graphene Quantum Dots/Graphene Hybrid Nanoplatelets as Efficient Electrocatalytic for Oxygen Reduction" in which Boron- and Nitrogen-Doped Graphene Quantum Dots/Graphene Hybrid Nanoplatelets were synthesized from anthracite coal by one-step chemical oxidation method (using $HNO_3$ and $H_2SO_4$) followed by codoping with nitrogen and boron at high-temperature annealing. The products were characterized by SEM, TEM, AFM, XPS, Raman analysis. This prior art mentioned about Boron- and Nitrogen-doped carbon dots. However, the method in the present invention is concerned with the carbon quantum dots.

Reference may be made to RSC Advances, 2014, 4 (81), 43160-43165 entitled "Chaos to order: an eco-friendly way to synthesize graphene quantum dots" in which highly ordered graphene quantum dots (GQDs) were synthesized by a rapid, simple and pollution-free method, which adopts cheap and readily available activated carbon but not coal and environmentally friendly hydrogen peroxide as raw materials through simple microwave and hydrothermal treatment. However, the present invention involves the usage of coal.

Reference may be made to Carbon, 2015, 93, 999-1007 entitled "Ethanol in aqueous hydrogen peroxide solution: Hydrothermal synthesis of highly photoluminescent carbon dots as multifunctional nanosensors" in which a novel synthetic strategy was developed for a facile, green and low-cost fabrication of highly photoluminescent carbon dots (C-dots) by hydrothermal treatment of ethanol in aqueous hydrogen peroxide ($H_2O_2$) solution. The products were characterized by TEM, XRD, Raman, XPS, FTIR, NMR, UV-visible, PL, and Time-resolved fluorescence analysis. However, the present invention adopts sono-chemical technique unlike the one reported in the art (hydrothermal treatment).

Reference may be made to U.S. patent application Ser. No. 14/888,301 which provides a method of making graphene quantum dots from a carbon source (e.g., coal and coke). The method includes exposure of the carbon source to an oxidant such as sulfuric acid ($H_2SO_4$) and nitric acid ($HNO_3$), sonicating the carbon source in the presence of the oxidant, heating the carbon source in the presence of oxidant at a temperature of 100-150° C. for 24-48 hrs. Thus, this patent reported the use of strong inorganic acids. However, ultrasonic assisted oxidation of coal was carried out in presence of $H_2O_2$ in the present invention, which makes it simple, facile, and faster. Moreover, there isn't any detailed product characterization reported in this patent with respect to their anti-bacterial, anti-algae and cytotoxic properties.

Reference may be made to U.S. patent application Ser. No. 14/836,826 which provides a method for preparing graphene quantum dot by sonication of a carbon material consisting of graphite, charcoal by using a fenton oxidant including, hydrogen peroxide. The method includes dispersing of the carbon material in an organic solvent, such as dimethylformamide followed by oxidizing the carbon material by adding the potassium peroxymonosulfate to the carbon material, and reducing the oxidized carbon material by performing a hydrothermal reaction. The inventors included the step of sono fenton and sono photo fenton reaction of carbon material to which potassium peroxymonosulfate has been added. However, the feed materials used in the reported art were graphite and charcoal unlike the present invention which uses coal. Also, different organic solvents were used in this patent application.

Reference may be made to CN104946252 which discloses a green, pollution-free method for extracting fluorescent carbon dots from coal. The method includes ball-milling of coal and water slurry to obtain a suspension of pulverized coal black followed by its oxidation in the presence of hydrogen peroxide and removing the hydrogen peroxide by heating. Further the supernatant liquor was cooled down and freeze-dried to get the fluorescent carbon dots. It was found that the carbon dots fluorescence yield was 40-60%. They formed point carbon size distribution 1-3 cnm and crystalline with defects. Although, this patent is quite similar with respect to the reagent ($H_2O_2$) used, yet the characteristics of the claimed CDTs produced are significantly different with the above. Also, the extraction method of CDTs adopted in the present invention is different. The art reports that the point carbon has the photocatalytic properties of degradation of methylene blue and methyl orange. However, they had not reported on the significant characteristics of CTDs such as higher florescence (FL) life time ($\tau$), higher molar absorption coefficient, higher quantum yield, anti-bacterial, anti-algae and cytotoxicity etc. Further, in the present invention the carbon source used is from low-quality high sulfur coal which is typically/chemically different and cheap from other coals. The method is advantageous over the prior art such as, less time consuming, minimum amount of water and ammonia solution is needed for the neutralization step and additional experimental steps is not required to enhance the yield of the product.

Reference may be made to Chinese Patent CN103803540 which provides a method for the preparation of graphene quantum dot from natural coal by ultrasonic treatment of mixture of pulverized coal and strong acid followed by adding hydrogen peroxide. The method includes mechanical crushing of the natural coal into different sizes powder followed by oxidation of pulverized coal with strong acid in an ultrasonic tank using Hummers method. Further, the reaction mixture was stirred overnight, centrifuged, neutralized and dialyzed to get the water soluble graphene quantum dots. However, in the present invention the carbon source used is from low-quality high sulfur coal which is typically/chemically different and cheap from other coals. The method is advantageous over the prior art such as, less time consuming, minimum amount of water and ammonia solution is needed for the neutralization step and additional experimental steps is not required to enhance the yield of the product.

Reference may be made to WO2016053411 which discloses scalable methods of producing carbon quantum dots from carbon sources with desired bandgaps by using oxidants like $H_2O_2$. However, the patent doesn't disclose anything about nature of the product characteristics such as antibacterial, antifungal, and cytotoxicity.

Reference may be made to "Multi-functional fluorescent carbon dots with antibacterial and gene delivery properties"; RSC Adv., 2015, 5, 46817-46822, DOI: 10.1039/C5RA07968C which evaluates the antibacterial activity of carbon dots on both gram positive and gram negative bacteria. However, the anticytotoxicity and antifungal characteristics of the carbon dots is nowhere reported in the prior art.

Reference may be made to patent WO 2014179708 A1 which recites a method of making graphene quantum dots from a carbon source, wherein the method comprises of exposing the carbon source to an oxidant, and the carbon source is selected from the group consisting of coal, coke and combinations thereof. Nevertheless, this reference only theoretically mentioned the usage of sub-bituminous coal and hydrogen peroxide as a carbon source and as an oxidant respectively, for the production of graphene quantum dots. But practically it was not verified. Also, it was found that the process is explosive, time-consuming and formation of sodium salts (NaNO3) take place during the neutralization step by sodium hydroxide or ammonia solution, which is difficult to separate from the reaction media. Moreover, large quantities of water are needed instead of sodium hydroxide and ammonia solution during the neutralization step. However, the present invention consumes less time, minimum amount of water and ammonia solution is needed for the neutralization step and additional experimental steps is not required to enhance the yield of the product. Further, in the present invention the carbon source used is from low-quality high sulfur coal which is typically/chemically different and cheap from other coals. The method is advantageous over the prior art such as, less time consuming, minimum amount of water and ammonia solution is needed for the neutralization step and additional experimental steps is not required to enhance the yield of the product.

Reference may be made to "Glowing Graphene Quantum Dots and Carbon Dots: Properties, Syntheses, and Biological Applications"; First published: 17 Dec. 2014; DOI: 10.1002/smll.201402648 which accounts for the enormous potential of carbon dots in the biomedical applications (lower cytotoxicity of the carbon dots against human cells due to their excellent biocompatibility), but the carbon dots was synthesized from carbon soots, graphite, 13C and Graphite, pitch-based carbon fibres, high purity graphite rod, and polystyrene by nitric acid oxidation, electroxidation, laser-ablated, acid treatment and chemical exfoliation, electrolysis, and electrochemical method respectively, not directly from low-quality high sulfur coal, which is typically/chemically different and cheap from other coals. Further, the present invention is simple and involves wet-chemical techniques with lesser steps. The product characteristics are also very much different.

In light of the existing prior arts, it may be summarized that the use of hydrogen peroxide and ultra-sonication method are known for the production of carbon dots and carbon quantum dots from carbon source other than low-quality Indian coal which is high in sulfur content. However, all these methods used expensive and high-quality raw materials (e.g. anthracite coal, graphite, activated carbon, coke etc.); highly demanding equipment and various steps are required to get the final desired product. Compared to the prior art, the present invention is easy to control, environmental friendly, simple preparation process, uses cheap raw material (i.e. low-quality high sulfur coal), and also suitable for large scale commercial production. Furthermore, the developed fabricated product of the present invention possesses higher quantum yield, is highly water soluble, emits blue-fluorescence with higher life time, and exhibits antimicrobial and cytotoxicity activity.

Thus, keeping in view the drawbacks of the hitherto reported prior arts, the inventors of the present invention realized that there exists a dire need to provide a process for the preparation of carbon dots which uses novel ultrasonic-assisted wet-chemical method, where only hydrogen peroxides ($H_2O_2$) is used as an oxidizing agent. The method also overcomes the above-mentioned drawbacks such as it is less time consuming, minimum amount of water and ammonia solution is needed for the neutralization step and additional experimental steps are not required to enhance the yield of the product. The prepared carbon dots were characterized by Scanning Electron Microscope (SEM), High Resolution-Transmittance Electron Microscope, X-ray powder Diffractometer, Thermal analysis, Laser micro-Raman system, FT-IR spectrophotometer, UV-Visible spectrophotometer, F-2700 FL Spectrophotometer, and Time-resolved photo-electron spectroscopy.

OBJECTIVES OF THE INVENTION

The main object of the present invention is thus to provide a process for the preparation of blue fluorescence emitting carbon dots from low-quality high sulfur sub-bituminous tertiary Indian coals by using ultrasonic-assisted wet-chemical method.

Another object of the present invention is to provide a process for producing value-added products (e.g. CQDT) from low-quality Indian coals.

SUMMARY OF THE INVENTION

The present invention provides a process for the preparation of blue-fluorescent emitting carbon dots from low-quality high sulfur sub-bituminous tertiary Indian coal by ultrasonic-assisted wet-chemical methods, wherein the said process comprises the following steps:
(a) pulverizing the sub-bituminous coals to 72 BS or 70 ASTM mesh size (0.211 mm) particles;
(b) mixing the pulverized coal obtained in step (a) with 20-30% $H_2O_2$ in ice cold condition wherein the rate of $H_2O_2$ addition to coal samples should be controlled by continuous stirring to minimize uncontrollable events;
(c) sonicating the mixture obtained in step (b) at room temperature for 5-6 hours to obtain a brown-red solution which was cooled down in an ice-water bath and slowly poured into a beaker containing about 500 ml of crushed ice;
(d) neutralizing the mixture obtained in step (c) by adding ammonia solution dropwise until the pH comes to 7;
(e) filtering the mixture obtained in step (d) through a 0.22-μm polytetrafluoroethylene membrane;
(f) dialyzing the filtrate obtained in step (e) in 1 kDa dialysis bag against ultrapure water for 5 days and collecting the solutions;
(g) concentrating the solutions obtained in step (f) using rotary evaporation to obtain the carbon dots and storing in ice-cold condition.

In an embodiment of the present invention, the carbon source is selected from the group consisting of low-quality sub-bituminous Indian coal having different carbon percentages.

In another embodiment of the present invention, the carbon source is selected from Northeast Indian coal.

In yet another embodiment of the present invention, the method comprises of exposing the carbon source to an environment friendly oxidant. The exposing results in the formation of the carbon dots.

In still another embodiment of the present invention, the oxidant used is hydrogen peroxide (20-30%).

In yet another embodiment of the present invention, the carbon source is exposed to an oxidant by sonicating the carbon source in the presence of an oxidant.

In still another embodiment of the present invention, the exposing comprises of heating the carbon source in the presence of the oxidant.

In yet another embodiment of the present invention, the method further comprises a step for separating the formed carbon dots from the oxidant.

In still another embodiment of the present invention, the separation occurs by neutralizing a solution comprising the formed carbon dots, filtering the solution, and dialyzing the solution.

In yet another embodiment of the present invention, the separation is done by filtration, washing with ultrapure water and the combination of such steps.

In still another embodiment of the present invention, the formed carbon dots have a crystalline structure.

In yet another embodiment of the present invention, the formed carbon dots have graphene quantum dots and carbon quantum dots.

In still another embodiment of the present invention, the formed carbon dots are functionalized with a plurality of functional groups, such as amorphous carbons, oxygen groups, carbonyl groups, carboxyl groups, esters, amines, amides, and combinations thereof.

In yet another embodiment of the present invention, the formed carbon dots comprise of oxygen addends or amorphous carbon addends on their edges.

In still another embodiment of the present invention, the fabricated carbon dots possess high quantum yield.

In yet another embodiment of the present invention, the carbon dots are water soluble and possess blue-fluorescence with higher life time.

In still another embodiment of the present invention, the carbon dots possess antimicrobial and cytotoxicity activity.

DETAILED DESCRIPTION OF THE INVENTION

The present invention provides a method of making carbon dots with novel characteristics from a carbon source, such as low-quality Indian coals. The method of the present invention involves: selecting the carbon sources, exposing the carbon sources to an oxidant to form carbon dots, and separating the formed carbon dots from the oxidant.

Coal Sources:

Various types of carbon sources may be utilized to form carbon dots. In some embodiments, the carbon source is Tertiary high sulphur coal. Coal is the most affordable, abundant and readily combustible energy resources being used worldwide. The chemical structure of coal is complex. The simplified composition contains angstrom or nanometer sized crystalline carbon domains with defects that are linked by aliphatic amorphous carbon. Although research on the nano-chemistry of coal has been initiated, but their practical application in electrical, mechanical and optical field is found to sparse. Consequently, coal is still mainly used as an energy source.

The structural characteristics of the coals create a perception that coal is only useful for producing energy through burning. The carbon-rich natural resource coal needs no longer to be burned only for the purpose of generating electricity but can be used as a feedstock to fabricate carbon material including carbon nanomaterials. Approximately one-third of the coal produced in the world, except for China, is low-quality. As a result, there is growing importance and demand for the utilization of low-quality coal. The low-quality coal needs to be cleaned before utilization. In this context, the different aspects of value addition to low-quality coals are very much essential. The inventors of the present invention have utilized low-quality coal for the first time to produce carbon dots. Various types of coals may be utilized as carbon source to form carbon dots. In some embodiments, the carbon source is sub-bituminous type coal of Tertiary age collected from Northeast region (NER) of India. In some embodiments, unique coal structure has advantages over pure $sp^2$ carbon allotropes for producing carbon dots. The use of additional carbon sources can also be envisioned.

Exposing the Carbon Sources to an Eco-Friendly Oxidant:

In some embodiments, carbon dots form by exposing the carbon source to an environment friendly oxidant. Various oxidants may be utilized to form carbon dots. In some embodiments, the oxidant includes Hydrogen Peroxide (20-30%), which is environment friendly. The utilization of hydrogen peroxide at different concentration can also be envisioned. The utilization of additional oxidant can also be envisioned.

Various methods may be utilized to expose carbon source to oxidants. The exposing occurs while the carbon source and the oxidant are in a liquid solution. In some embodiments, the exposing includes sonicating the carbon source in the presence of the oxidant. In some embodiments, the exposing includes stirring the carbon source in the presence of the oxidant. In some embodiments, the sonicating occurs for 6 hrs. In some embodiments, the sonication time may increase or decrease depending upon the carbon source. In some embodiments, the oxidant may be exposed to the carbon source in a slow manner. For instance, in some embodiments, the oxidant is mixed dropwise with the carbon source under ice cold conditions. Additional methods of exposition of carbon sources to oxidants can also be envisioned.

The exposure of carbon sources to oxidants followed by sonication can lead to the formation of carbon dots. Without being formed by the theory, inventors envision that upon the exposure of coal to oxidants followed by sonication, carbon dots form by exfoliation of the carbon source. In particular, inventors envision that the crystalline carbon within the coal structure was oxidatively displaced to form carbon dots.

Separation of Carbon Dots:

The method of the present invention includes a step of separating the formed carbon dots from the oxidants such as $H_2O_2$. Separating includes neutralizing a solution that contains the formed carbon dots by ammonia solution, filtering the solution and dialysis of the solution. In some embodiments, the separating steps include dialysis of the solution that contains the formed carbon dots. Additional methods of separating carbon quantum dots from oxidants can also be envisioned.

EXAMPLES

The following examples are given by way of illustration only and therefore should not be construed to limit the scope of the present invention in any manner.

Example 1: Fabrication of Carbon Dots from Tertiary Indian Coal (Sub-Bituminous Rank)

In this example, there is provided a facile approach for producing carbon dots from sub-bituminous rank coal. The synthesized carbon dots from coal in a cost-effective manner are water soluble and fluorescent in aqueous solution. In this example, an inexpensive facile one-step wet-chemistry route was used to synthesize/produce carbon dots from carbon sources of four different types of sub-bituminous rank Northeast Indian coals: Tirap-60, Tirap-20, Coal-NK, and coal-NG. The physico-chemical characteristics of the coal samples used in the investigation are shown in Table 1.

TABLE 1

| Physico-chemical characterization of the coal samples (as received basis, wt %) | | | | | | | |
|---|---|---|---|---|---|---|---|
| SL No | Coal Samples | Proximate analysis (%) | | | Ultimate analysis (%) | | TS (%) |
| | | M | Ash | VM | FC | C | H | |
| 1. | TD-T60 | 2.20 | 2.95 | 45.02 | 49.82 | 80.40 | 5.97 | 3.62 |
| 2. | TD-T20 | 2.35 | 2.33 | 50.27 | 45.05 | 80.90 | 8.19 | 1.90 |
| 3. | TD-NK | 3.82 | 19.04 | 36.32 | 40.83 | 61.20 | 5.86 | 3.26 |
| 4. | TD-NG | 9.11 | 4.44 | 49.07 | 37.38 | 67.50 | 7.31 | 3.59 |

M: Moisture;
Ash: Ash content;
VM: Volatile Matter;
FC: Fixed Carbon;
C: Carbon;
H: hydrogen;
N: Nitrogen;
TS: Total Sulphur The specific methodologies used for the synthesis of carbon dots are summarized herein:

Example 1.1 Synthesis/Production of Carbon Dots from Coal Sample (Tirap-60)

12 g of coal sample was mixed with 200 ml hydrogen peroxide (20-30%) under ice-cold condition. The reaction mixture was then sonicated (frequency: 20-40 kz, output power: 700-1000 W) in a microprocessor-based bench type ultrasonic bath for 3-6 hrs at atmospheric pressure and temperature. The solution was cooled to room temperature and poured into a beaker containing 500 ml crushed ice followed by addition of ammonium solution until the pH was 7. The neutral mixture was then filtered through a 0.22-μm polytetrafluoroethylene membrane and filtrate was dialyzed in 1 kDa dialysis bag for 5 days. After purification, the solution was concentrated using rotary evaporation and the carbon dots solution was collected. The synthesized carbon dot is denoted as Coal-T60-CDTs in the subsequent part of the description.

Example 1.2 Fabrication of Carbon Dots from Coal Samples (Tirap-20)

The same experimental procedure as outlined in Example 1.1 was conducted with Tirap-20 coal sample in the same manner. The synthesized carbon dot is denoted as Coal-T20-CDTs.

Example 1.3 Fabrication of Carbon Dots from Coal Samples (Coal-NK)

The same experimental procedure as outlined in Example 1.1 was conducted with Coal-NK in the same manner. The synthesized carbon dot is denoted as Coal-NK-CDTs.

Example 1.4 Fabrication of Carbon Dots from Coal Sample (Coal-NG)

The same experimental procedure as outlined in Example 1.1 was conducted with the Coal-NG in the same manner. The synthesized carbon dot is denoted as Coal-NG-CDTs.

The concentration of the as-synthesized carbon dots was calculated by using Thermal Analyzer and estimated to be about 7.4 mg/ml (Coal-T20-CDTs), 4.4 mg/ml (Coal-NK-CDTs), 4.2 mg/ml (Coal-NG-CDTs), and 2.4 mg/ml (Coal-T60-CDTs).

The microstructure/nanostructure of the synthesized carbon dots was investigated by using transmission electron microscope (TEM/HRTEM). The diameters of these fabricated carbon dots were estimated to be in the range of 1-6 nm, 2-5 nm, 10-30 nm, and 1-4 nm for Coal-T60-CDTs, Coal-T20-CDTs, Coal-NK-CDTs, and Coal-NG-CDTs respectively, which revealed the formation of carbon quantum dots (CQDTS) as well as graphene quantum dots (GQDTS). In some embodiments, the formed carbon quantum dots and graphene quantum dots had a crystal structure. In some embodiments, the formed graphene quantum dots had single layer to multiple layers. In some embodiments, the formed carbon quantum dots and graphene quantum dots included amorphous carbon addends on their edge.

The FTIR analysis of the synthesized carbon dots showed the presence of C=C, C—O, C=O, H—C, and O—H vibration modes. The intensity of the C—O, C=O and O—H vibrations modes was found to be increased, owing to the introduction of hydrophilic functionalities and consequently, the carbon dots showed high solubility in water.

The Raman spectra of the carbon dots showed mainly two characteristic bands appearing at 1616 cm$^{-1}$ (G-band) and 1375 cm$^{-1}$ (D-band) for Coal-T60-CDTs; 1553 cm$^{-1}$ (G-band) and 1381 cm$^{-1}$ (D-band) for Coal-T20-CDTs; 1553 cm$^{-1}$ (G-band) and 1382 cm$^{-1}$ (D-band) for Coal-NK-CDTs; 1595 cm$^{-1}$ (G-band) and 1387 cm$^{-1}$ (D-band) for Coal-NG-CDTs. The G-band originated from the vibration of the sp$^2$-hybridized carbon framework in the 2D hexagonal lattice of graphite cluster and D-band originated from a lattice defect including the sp$^a$ hybridized carbon. The G-bands correspond to the first-order scattering of the $E_{2g}$ stretching mode of graphite. The D-band is due to the residual ill-organized graphite.

The photo-physical properties of the carbon dots were investigated by using ultraviolet (UV-vis) spectroscopy, FL spectroscopy, and time-resolved single-photon counting spectroscopy. The fabricated carbon dot was excited at 300 nm and the corresponding ultraviolet absorption was observed. The absorption bands appeared at around 220-300 nm and were due to the excitation of pi-electrons (π→π*) of the aromatic n system. The molar absorption coefficient (ε) of the blue-emitting Carbon Dots was estimated to be about 5662.50 M$^{-1}$cm$^{-1}$ (Coal-NG-CDTs), 18716.25 M$^{-1}$cm$^{-1}$ (Coal-NK-CDTs), 10500 M$^{-1}$cm$^{-1}$ (Coal-T60-CDTs), and 22500 M$^{-1}$cm$^{-1}$ (Coal-T20-CDTs). The emission maximums of carbon dots solution were at around 460 nm, corresponding to the blue fluorescence. The fluorescence blue colour of the synthesized carbon dots was revealed at 365 nm under UV-lamp.

The time-resolved single-photon counting spectroscopy of the synthesized carbon dots was observed at neutral pH. The corresponding FL life time (τ), calculated by fitting to exponential using iterative reconvolution, are summarized in Table 2. The observed $τ_1$ (<0.8 ns, <1.00 ns, <0.9 ns, and <0.7 ns) for Coal-T60-CDTs, Coal-T20-CDTs, Coal-NK-CDTs, and Coal-NG-CDTs respectively are thought to be due to the photoluminescence decay of the aggregated state. The life times $τ_3$ (>10 ns, >9 ns, >8 ns, and >8 ns) for Coal-T60-CDTs, Coal-T20-CDTs, Coal-NK-CDTs, and Coal-NG-CDTs respectively were longer in comparison to the ones reported earlier, which accounts for the higher PL emission.

TABLE 2

Life time (τ) calculated from the time-resolved decay profile of the synthesized carbon dots (CDTS).

| Samples | $τ_1$ (ns) | $f_1$ | $τ_2$ (ns) | $f_2$ | $τ_3$ (ns) | $f_3$ | Avg τ |
|---|---|---|---|---|---|---|---|
| Coal-T60-CDTs | 0.791 ± 0.088 | 15.84 | 2.747 ± 0.028 | 19.51 | 10.139 ± 8.7e−4 | 64.65 | 4.55 |
| Coal-T20-CDTs | 0.992 ± 0.069 | 19.49 | 3.520 ± 0.017 | 31.60 | 9.982 ± 0.002 | 48.91 | 4.83 |
| Coal-NK-CDTs | 0.870 ± 0.067 | 23.02 | 3.340 ± 0.021 | 34.00 | 8.873 ± 0.004 | 42.98 | 4.36 |
| Coal-NG-CDTs | 0.626 ± 0.156 | 16.37 | 2.453 ± 0.018 | 39.32 | 8.105 ± 0.002 | 44.30 | 3.72 |

Quantum Yield of the Carbon Dots:

The quantum yield of the as-fabricated coal-derived carbon dots were calculated with the following formula:

$$\phi = \phi r \times I/Ir \times Ar/A \times \eta/\eta r$$

wherein, φ is the relative quantum yield with respect to the reference/standard. In the present invention, 0.1 mg/L Quinine Sulfate in 0.1M $H_2SO_4$ solution was used as standards. "I" is the measured integrated emission intensity, η is the refractive index of the solvent, and A is the optical density (absorbance). The subscript R refers to standard index of the Quinine Sulfate.

In the present invention, the FL quantum yield of the as-fabricated carbon dots was calculated to be about 3% (Coal-T20-CDTs), 4% (Coal-NK-CDTs), 8% (Coal-T60-CDTs), and 14% (Coal-NG-CDTs). These are quite higher than the other CDTs reported in prior art. In some embodiments, the quantum yield may vary depending upon the carbon source.

Example 1.5

Antimicrobial, Antifungal, and Cytotoxicity Test of the Fabricated Carbon Dots

As the proposed method for the fabrication of carbon dots from coals completely avoids the use of toxic materials and reagents, the Antimicrobial, Antifungal, and Cytotoxicity test for their biocompatibility and bio-labelling application were also investigated.

Antimicrobial and Antifungal Test:

The antimicrobial activity of the as-fabricated carbon dots was tested against five bacterial species [gram negative: *Pseudomonas aeruginosa* (MTCC2453), *Escherichia coli* (MTCC739), and gram positive: *Mycobacterium abscessus* (ATCC19977), *Staphylococcus aureus* (MTCC96) and *Bacillus subtilis* (MTCC441)] and two fungal species [*Candida albicans* (MTCC3017) and *Fusarium oxysporum*(N-CIM1281)] respectively. For the activity assessment, 100 µl of each of the bacterial and fungal culture was inoculated in Nutrient agar plates and potato dextrose agar plate using spread plate method, respectively. In each plate, four 6-mm wells were prepared using sterilized cork-borer and 50 µl of each test sample was inoculated in it. The as prepared bacterial and fungal plates were then incubated at 35° C. for 24 h and 28° C. for 5 days respectively. Finally, the inhibition zone (mm) was recorded. It was observed that 50 µl of the as-fabricated carbon dots do not inhibit the growth of any bacterial and fungal strains.

Cytotoxicity Test:

The commercially available cell Lines namely, L6 (Rat muscle cell line), HeLa (Human cervical cancer cell line), PC3 (Human prostate cancer cell line) and MDAMB 231 (Human breast adenocarcinoma cell line) procured from NCCS, Pune and cultured in respective complete media (DMEM for L6 and MDA-MB-231, MEM for HeLa, and Ham's F12k for PC3) supplemented with 10% Fetus Bovine Serum (FBS), 10% Penstrep, 1% Gentamycin were incubated under standard conditions in 37° C. humidified 5% $CO_2$ atmosphere. After reaching confluence ($1\times10^6$ cells per ml) cells were seeded in tissue culture grade 4-well Millicell EZ Slide (Millipore) in complete medium and incubated. After 24 hrs, the complete medium was replaced with FBS free medium and incubated overnight. The cells were then treated with planned amount of the as-fabricated carbon dots into each well and incubated for 3 h. Cell maintained in sample free medium served as control. After the treatment, the cells were washed 3 times with phosphate buffer to remove any particles not taken up by the cell. The slide was removed from the holder and mounted with fluoroshield (Sigma). The mounted slide was checked under a fluorescent microscope (Motic AE31) and image of the cells captured with excitation at 490 and 557 nm.

After treatment, all the cells were attached with the slide and no change in the morphology of the cells were detected against control. Cell Viability (MTT) Assay of as-fabricated carbon dots in HeLa cell line induced moderate cell death in a dose-dependent manner.

After 3 h incubation, the survival rate was higher than 70% even if the concentration of the as-fabricated carbon dots was increased up to 24 µg/mL (Coal-T60-CDTs), 44 µg/mL (Coal-NK-CDTs), 42 µg/mL (Coal-NG-CDTs), and 74 µg/mL (Coal-T20-CDTs), which indicates the fairly low toxicity of the as-fabricated carbon dots. Next, cell imaging was performed on a fluorescence microscope after incubating L6 cell line with the planned amount of as-fabricated carbon dots for 3 h. The bright field image showed that the treated cell retained their original fusiform morphology, which also confirmed the low toxicity of the as-fabricated carbon dots. FITC image, TRITC image, and merged image showed that L6 cells labelled by as-fabricated carbon dots shine under UV-radiation which further indicated that the developed carbon dots could be used as a promising material for optical-imaging/bio-imaging.

In summary, the present invention concerning "coal-derived blue fluorescence emitting carbon dots (CDTs)" from low-quality Tertiary Indian high sulphur coals, compared to the existing prior arts, have significant molar absorption coefficient, higher FL life time, and higher Quantum Yield ($\phi$) in the range of 5662-22500 $M^{-1}$ $cm^{-1}$, 8-10 ns, and 3-14% respectively. Furthermore, the non-toxicity of the coal-derived CDTs to bacterial and fungal strains; and also anticytotoxic activity against human cells was observed.

TABLE 3

Summary of the characteristics of as-synthesized blue-emitting carbon dots from Indian coals

| Carbon dots | Concentration (mg/mL) | molar absorption coefficient ($\epsilon M^{-1} cm^{-1}$) 240 nm) | FLlife time ($\tau$)(ns) | Quantum Yield ($\Phi$) (%) |
|---|---|---|---|---|
| Coal-T20-CDTs | 7.4 | 22500.00 | >9 | 3 |
| Coal-NK-CDTs | 4.4 | 18716.00 | >8 | 4 |
| Coal-NG-CDTs | 4.2 | 5662.00 | >8 | 14 |
| Coal-T60-CDTs | 2.4 | 10500.00 | >10 | 8 |

ADVANTAGES OF THE INVENTION

Typical blue-emitting carbon dots (as summarized above) can be produced by a simple and environmentally benign method.

The low-quality Indian coal could be converted into highly value-added product like carbon dots (CDTs).

Hydrogen peroxide is used as oxidizing agent instead of mineral acid solution (conc. $H_2SO_4$ and $HNO_3$) as reported elsewhere, which is highly explosive and difficult to handle during large scale production.

The method is less time consuming than the reported methods in the art.

Neutralization step is simple. Large volume of water is not required for neutralization step as reported in the art.

We claim:

1. A process for the preparation of blue-fluorescence emitting carbon dots (CDTs) from a carbon source, wherein the carbon source is sub-bituminous tertiary high sulfur coals, wherein the process comprising the steps of:
   a) pulverizing the sub-bituminous tertiary high sulfur coals to 72 BS or 70 ASTM mesh size (0.211 mm) particles;
   b) mixing the pulverized coal obtained in step (a) with 20-30% of an oxidant under ice cold condition, wherein the oxidant is hydrogen peroxide;
   c) sonicating the mixture obtained in step (b) at room temperature for 6 hours to obtain a brown-red solution and cooling it in an ice-water bath followed by slow pouring into a beaker containing 500 ml of crushed ice;
   d) neutralizing the mixture obtained in step (c) by adding ammonia solution dropwise until pH 7 is attained;
   e) filtering the neutralized mixture obtained in step (d) through 0.22-µm polytetrafluoroethylene membrane;
   f) dialyzing the filtrate obtained in step (e) in 1 kDa dialysis bag against ultrapure water for 5 days and collecting the solutions;
   g) concentrating the solutions obtained in step (f) using rotary evaporation to obtain the desired carbon dots and storing under ice-cold condition.

2. The method as claimed in claim 1, wherein the carbon source is selected from sub-bituminous tertiary high sulfur coal having different percentages of carbon.

3. The method as claimed in claim 1, wherein the carbon source comprises low-quality coal.

4. The method as claimed in claim 1, wherein the sonication frequency is 20-40kz and output power is 700-1000W in a microprocessor based bench type ultrasonic bath.

5. The method as claimed in claim 1, wherein the formed carbon dots have diameter ranging from 1-6 nm.

6. The method as claimed in claim 1, wherein the formed carbon dots are crystalline and functionalized with a plurality of functional groups selected from amorphous carbon, oxygen group, crystal group and carboxyl group.

7. The method as claimed in claim 1, wherein the formed carbon dots comprise carbon quantum dots as well as graphene quantum dots.

8. The method as claimed in claim 1, wherein the formed carbon dots emit blue fluorescence.

9. The method as claimed in claim 1, wherein the sub-bituminous tertiary high sulfur coal is from India.

10. The method as claimed in claim 1, wherein the formed carbon dots have diameter ranging from 2-5 nm.

11. The method as claimed in claim 1, wherein the formed carbon dots have diameter ranging from 10-30 nm.

12. The method as claimed in claim 1, wherein the formed carbon dots have diameter ranging from 1-4 nm.

13. The blue-fluorescence emitting carbon dots obtained by the process as claimed in claim 1 useful in optical-imaging and bio-sensing including road stickers, road signs, paints, photographic processing materials and the like.

* * * * *